United States Patent
Oku et al.

(10) Patent No.: US 8,940,715 B2
(45) Date of Patent: Jan. 27, 2015

(54) LIPID-REGULATING AGENT AND USE THEREOF

(75) Inventors: Kazuyuki Oku, Okayama (JP); Michio Kubota, Okayama (JP); Shigeharu Fukuda, Okayama (JP); Toshio Miyake, Okayama (JP)

(73) Assignee: Hayashibara Co., Ltd., Okayama (JP)

( * ) Notice: Subject to any disclaimer, the term of this patent is extended or adjusted under 35 U.S.C. 154(b) by 1413 days.

(21) Appl. No.: 12/033,654

(22) Filed: Feb. 19, 2008

(65) Prior Publication Data

US 2008/0214499 A1    Sep. 4, 2008

Related U.S. Application Data

(62) Division of application No. 10/551,765, filed as application No. PCT/JP2004/004079 on Mar. 24, 2004, now abandoned.

(30) Foreign Application Priority Data

Apr. 3, 2003  (JP) ................................. 2003-100408

(51) Int. Cl.
| | | |
|---|---|---|
| A61K 31/702 | (2006.01) | |
| A61K 31/575 | (2006.01) | |
| A23D 9/007 | (2006.01) | |
| A23K 1/16 | (2006.01) | |
| A23L 1/30 | (2006.01) | |
| C07H 3/06 | (2006.01) | |

(52) U.S. Cl.
CPC .............. *A23D 9/007* (2013.01); *A23K 1/1643* (2013.01); *A23L 1/30* (2013.01); *A61K 31/702* (2013.01); *C07H 3/06* (2013.01)
USPC ............................................ 514/61; 514/171

(58) Field of Classification Search
USPC .................................................. 514/61, 171
See application file for complete search history.

(56) References Cited

U.S. PATENT DOCUMENTS

| 5,786,196 A | 7/1998 | Cote et al. |
| 7,192,746 B2 | 3/2007 | Kubota et al. |

FOREIGN PATENT DOCUMENTS

| EP | 1 460 081 A | | 9/2004 | |
|---|---|---|---|---|
| JP | 60094912 A | * | 5/1985 | ............ A61K 31/715 |
| JP | 07115934 A | * | 5/1995 | ................ A23L 1/30 |
| JP | 08283154 A | * | 10/1996 | ............. A61K 31/35 |
| WO | WO 01/90338 | | 11/2001 | |

OTHER PUBLICATIONS

Coats, AJ. Postgrad. Med. J., 1998, 74, p. 391-394.*
Machine translation of JP 08-283154 A, http://dossier1.ipdl.inpit.go.jp, accessed online on Aug. 16, 2010.*
Ros, E. Atherosclerosis, 2000, 151, p. 357-379.*

(Continued)

*Primary Examiner* — Eric Olson
*Assistant Examiner* — Jonathan S Lau
(74) *Attorney, Agent, or Firm* — Browdy and Neimark, P.L.L.C.

(57) ABSTRACT

The object of the present invention is to provide a lipid-regulating agent or a composition for regulating the amount of lipids comprising the agent. The present invention solves the above object by providing a lipid-regulating agent comprising a cyclic tetrasaccharide and/or its saccharide-derivative(s) and a composition for regulating the amount of lipids comprising the lipid-regulating agent.

2 Claims, No Drawings

(56) References Cited

OTHER PUBLICATIONS

Riottot et al., Lipids, 1993, 28, p. 181-188.*
Entry for high blood cholesterol levels, MedlinePlus, www.nlm.nih.gov/medlineplus/ency/article/000403.htm, accessed online on Nov. 8, 2013.*
Nakayama et al., Japan. J. Pharmacol., 1987, 44, p. 135-143.*
AIPN machine translation of JP 07-115934, http://dossier1.ipdl.inpit.go.jp/, accessed online on May 29, 2014.*
Artiss et al., Metabolism Clinical and Experimental, 2006, 55, p. 195-202.*
G.L. Coete et al, "Enzymically produced cyclic alpha-1,3-linked and alpha-1,6-linked oligosaccharides of D-Glucose", *European Journal of Biochemistry,* Berlin, DE, vol. 226, 1994 pp. 641-648, XP002945423, ISSNP: 0014-2956.
P. Biely et al, "Enzymic alpha-galactosylation of a cyclic glucotetrasaccharide derived from alternan", *Carbohydrate Reseach,* Elsevier Scientific Publishing Company, Amsterdam, NL, vol. 332, No. 3, 4, pp. 299-303, XP004249620, Jun. 2001, ISSN: 008-6215.
Aga, Hajime et al, "Production of Cyclic Tetrasaccharide from Starch Using a Novel Enzyme System from *Bacillus globisporus* C11", *Journal of Bioscience and Bioengineering,* 94(4), 336-342 CODEN: JBBIF6: ISSN: 1389-1723, 2002, XP002408856.
Delzenne et al. Am. J. Nutr 2001, 73, 456S-8S.

* cited by examiner

LIPID-REGULATING AGENT AND USE THEREOF

RELATED APPLICATION

This is a divisional of U.S. application Ser. No. 10/551,765, filed Oct. 3, 2005, which said application is a national phase of international application PTO/JP2004/004079, filed Mar. 24, 2004.

TECHNICAL FIELD

The present invention relates to a novel lipid-regulating agent and use thereof, particularly, to a novel lipid-regulating agent comprising a non-reducing saccharide where four glucose molecules are bound via alternating α-1,3 and α-1,6 linkages, i.e., a cyclic tetrasaccharide, represented by the formula of cyclo {→6)-α-D-glucopyranosyl-(1→3)-α-D-glucopyranosyl-(1→6)-α-D-glucopyranosyl-(1→3)-α-D-glucopyranosyl-(1→} (hereinafter, simply abbreviated as "CTS" in this specification), and/or its saccharide-derivative(s) as an effective ingredient(s), and to a composition for regulating the amount of lipids, comprising the lipid-regulating agent.

BACKGROUND ART

In recent years, accompanying with the progress in living standard, dietary habits have altered to Western-style in many countries including Japan. Therefore, we tend to intake excess calories and lipids compared with a traditional dietary habit. As a result, patients and potential patients of lifestyle-related diseases such as hyperlipemia, cholesteremia, diabetes, hypertension, adiposis, etc. have increased. Among those, adiposis, which is caused by the excess increase of lipids in the living body, is a risk factor of those lifestyle-related diseases and is recognized as a large problem on human health. Furthermore, adiposis is a risk factor of hyperlipemia, cholesteremia, cardiovascular disease, hepatic disease, malignant tumor, diabetes, etc. and is suggested to involve the crisis and the aggravation of gout, cholecystolithiasis, etc.

Particularly, in Japanese society which is on the way of an aging society, the prevention of adiposis is highlighted as an important object from a viewpoint of preventive medicine because adiposis is a risk factor of lifestyle-related diseases. Also, women in and/or after adolescence tend to hate the corpulence. Some of them get out of order of hormone valance and cause critical diseases such as osteoporosis by the diet with wrong methods, causing excess burden on the body.

Usually, a method for limiting calories by ingesting low-fat or low-calorie foods and that for burning off calories by aerobic exercises are recommended as a means of curing or preventing adiposis and hyperlipemia. However, many people are forced to abandon such methods because they require pointed leadings and a long period. Also, the dietary restriction is not preferable from the viewpoint of mental health. Although taking drugs is effective for curing or preventing adiposis and hyperlipemia, the side-effect and cost of the drugs cause problems.

It is particularly desirable for patients and potential patients of diseases such as adiposis, hyperlipemia, cholesteremia, etc., to prevent such diseases effectively with taking delicious and safe foods, snacks, and healthy foods in a daily eating habit. Under these circumstances, the development of effective materials for curing or preventing adiposis, hyperlipemia, cholesteremia, diabetes, etc., which show delicious taste intact or in combination of other foods, is now in progress. Recently, accompanying with the recent health fad or the establishment of health-promoting foods such as foods specified health use, general public rise awareness for curing and preventing adiposis, hyperlipemia, cholesteremia, diabetes, etc., by ingesting foods and beverages. Under these circumstances, many food materials such as fats including diacylglycerols and plant sterols, which inhibit uptake of fats and cholesterols; and low-calorie sweeteners including synthetic highly-sweetened sweeteners and sugar alcohols are already commercialized. For example, lipid-reducing agents, comprising saccharides such as xyloglucan, agarooligosaccharide, etc., as effective ingredients, are disclosed in Japanese Patent Kokai Nos. 147,934/95, 224,608/97, and 349,485/99. Further, a lipid-metabolism-improving agent, comprising substances such as hesperetin, naringenin, etc., as effective ingredients, are disclosed in Japanese Patent Kokai No. 280, 358/96. Furthermore, in "*SHOKUMOTSU-SENI KISO-TO-OYO* (Dietary fiber, its basis and application)" published by ASAKURA-SHOTEN in 1997, it is disclosed that dietary-fifers represented by cellulose or gummy substances involve in the metabolism of lipids, bile acids, and cholesterols and have an activity of improving lifestyle-related diseases. However, in the case of using those ingredients for materials of foods and beverages, some of those ingredients are food materials having disadvantages of deteriorating the taste, flavor, and mouthfeel; being not effective without taking in a relatively large amount; or causing diarrhea depending on the physical condition or the predisposition. To meet the recent diversified eating habit, it is desirable to develop food materials having a safety and activity of preventing or treating diseases such as adiposis, hyperlipemia, cholesteremia, diabetes, etc., without causing the deterioration of taste, flavor, and mouthfeel even when one takes it habitually.

While, the applicant of the present invention disclosed a novel process for producing CTS and/or a saccharide composition comprising CTS and its saccharide-derivative(s), and a composition comprising those saccharides in International Publication Nos. WO 01/090,338, WO 02/010,361, and WO 02/072,594. Also, the applicant of the present invention disclosed in those specifications that those saccharides are hardly metabolized by intestinal bacteria and have a dietary fiber-like activity. However, in all those literatures, there is no disclosure about the lipid-regulating activity of CTS and/or its saccharide-derivative(s) or a composition comprising those saccharides.

DISCLOSURE OF INVENTION

The first object of the present invention is to provide a lipid-regulating agent for preventing or improving the increase or the accumulation of lipids, which is taken from foods and beverages or synthesized in a living body, in blood or in tissues and organs in a living body. The second object of the present invention is to provide a composition for regulating the amount of lipids, comprising the lipid-regulating agent.

To solve the above objects, the present inventors have studied on a lipid-regulating agent comprising a saccharide as an effective ingredient for a long period of time. As a result, the present inventors found that CTS and/or its saccharide-derivative(s) effected on the regulation of the amount of lipids, and then inhibits the increase of body weight, and regulates the amount of cholesterol to the ordinary level or very close to it. The present inventors accomplished the present invention by establishing a novel lipid-regulating agent and a composition for regulating the amount of lipids, comprising the lipid-regulating agent.

BEST MODE FOR CARRYING OUT THE INVENTION

The saccharide-derivative of CTS as referred to as in the present invention means a saccharide where one or more glycosyl residues are bound to CTS, and the glycosyl residues include one or more kinds of glycosyl residue, for example, a saccharide where one or more glucose molecules are bound to one or more hydroxyl groups of CTS, which is obtained by allowing α-isomaltosylglucosaccharide-forming enzyme and α-isomaltosyl-transferring enzyme to act on starch. In addition, such saccharides include those which one or more glycosyl residues such as α-D-glucopyranosyl residue, β-D-galactopyranosyl residue, and β-D-chitosaminyl residue are transferred to one or more hydroxyl groups of CTS and/or a saccharide-derivative of CTS described above. The saccharide-derivatives of CTS are obtainable by allowing one or more saccharide-transferring enzymes such as cyclomaltodextrin glucanotransferase, β-galactosidase, α-galactosidase, lysozyme, etc., to act on their substrates such as monosaccharides, oligosaccharides and/or polysaccharides in the presence of CTS and/or its saccharide-derivative(s) according to the method disclosed by the inventors of the present invention in International Publication No. WO 02/072,594. Further, saccharides, prepared by transferring one or more glycosyl residues such as α-D-glucopyranosyl residue, β-D-galactopyranosyl residue, β-D-chitosaminyl residue, etc., to glycosyl residues including α-D-glucopyranosyl residue, β-D-galactopyranosyl residue, and/or β-D-chitosaminyl residue of saccharide-derivatives of CTS, can be arbitrarily used.

CTS and its saccharide-derivatives usable in the present invention are not restricted by their origins and processes, and they can be produced by fermentation method, enzymatic method, and organic synthesis. The reaction mixture obtainable by the above methods can be used intact as CTS and its saccharide-derivatives, or used as a solution thereof. The reaction mixture can be partially or highly purified by using ion-exchange resins to remove impurities. Also, mixtures of CTS and one or more saccharide-derivatives of CTS can be arbitrarily used in the present invention. CTS and its saccharide-derivatives can be produced from amylaceous substances or saccharides inherent to the enzymatic methods such as a method for converting panose into CTS by α-isomaltosyl-transferring enzyme, disclosed by the same applicant as the present invention in International Publication No. WO 01/090,338, and a method for producing CTS from starch by using α-isomaltosylglucosaccharide-forming enzyme and α-ismaltosyl-transferring enzyme in combination, disclosed in International Publication No. WO 02/010, 361. CTS and its saccharide-derivatives can be also produced by the method disclosed by the same applicant as the present invention in International Publication No. WO 02/072,594. These methods can be used for producing CTS and its saccharide-derivatives in a high efficiency and a lower cost using starch as an abundant and low cost material. Therefore, CTS and its saccharide-derivatives can be advantageously produced on an industrial scale. CTS has a form of anhydrous amorphous, anhydrous crystalline, crystalline monohydrate, or crystalline pentahydrate, and any of which can be used in the present invention. Among these, CTS in an anhydrous crystalline, crystalline monohydrate, or anhydrous amorphous form has a satisfactory dehydrating activity and it can be used to powderize or solidify hydrous substances as a dehydrating agent by admixing with a hydrous substance such as unsaturated compounds. Therefore, CTS in such a form can be advantageously used for producing a high quality powder or solid product, comprising CTS as an effective ingredient.

Lipids, which can be regulated by the lipid-regulating agent of the present invention, include homolipids, heterolipids and induced lipids in living bodies; concretely, homolipids such as neutral fats including triglycerides; heterolipids such as glycerophospholipids, glyceroglycolipids, sphingophospholipids, and sphingoglycolipids; heterolipids such as lipoproteins including high-density lipoprotein cholesterol (HDL-cholesterol), low-density lipoprotein cholesterol (LDL-cholesterol), and remnant-like lipoprotein cholesterol; and lipoproteins in cellular membrane; induced lipids such as saturated fatty acids including stearic acid and palmitic acid; unsaturated fatty acids including α-linoleic acid and α-linolenic acid; and free fatty acids including multiple unsaturated fatty acids, fatty alcohols, steroids, and cholesterols. In this specification, the sum of cholesterols, contained in serum lipoprotein, such as high-density lipoprotein cholesterol, low-density lipoprotein cholesterol, and remnant-like lipoprotein cholesterol, and free cholesterols in blood may be called as "total cholesterol".

It is generally well known that lipids in a living body increase in body fluids including blood and are accumulated as subcutaneous fats or visceral fats in or around various visceral organs such as testicle, kidney, heart, liver, gastrointestinal tract, due to metabolic disorder or excess intake of foods. The term "the regulation of lipids" as referred to as in the present invention means inhibiting the accumulation of lipids in a living body, reducing those lipids in a living body to a normal level, and keeping them in the normal level. The term "the regulation of lipids" also means reducing cholesterols and triglycerides deposited to blood vessel wall as observed in the case of arterial sclerosis.

The term "lifestyle-related diseases" as referred to as in the present invention means chronic diseases caused by excess accumulation of lipids, concretely, hyperlipemia, asterioscle-rosis, angiostenosis, vascular obstruction, hypertention, increase of blood adhesiveness, formation of thrombus, angina, cardiac infarction, cardiac incompetence, brain infenction, fatty liver, cirrhosis, adiposis, constipation, malignant tumor such as hepatoma and tumor of large intestine, diabetes, and various diseases accompanied by the above diseases.

The lipid-regulating agent of the present invention can be used for domestic animals including cattle, pig, etc.; poultry including chicken, duck, etc.; cultivated fish and shellfish such as bream, flatfish, young yellowtail, and clam; cultivated crustacean such as shrimp, crab, etc.; insects including silkworm, honeybee, etc.; and pets including dogs, cats, birds, etc., as well as for humans. The lipid-regulating agent of the present invention can be used for regulating the increase of lipids in living bodies of animals including human, caused by excess intake of foods and feeds and by congenital or acquired metabolic disorders. Further, the lipid-regulating agent of the present invention can be arbitrarily used for reducing lipids of animals even in the case of the index value being in a normal range, as well as those in the case of lifestyle-related disease such as adiposis, hyperlipemia, cholesteremia, etc., being caused by the increase of lipids in a living body.

The "corpulence" as referred to as in the present invention means, in the case of human, one whose body mass index (BMI), a value calculated by dividing two times one's weight (kg) by one's body height (m), which is a criterion used in Japan Society for the Study of Obesity, of higher than 25. Even in the case of being BMI of 25 or lower, one whose amount of lipids of specific parts such as tissues and visceral organs is higher than the normal level is classified into "corpulence" in the present invention. For example, one whose visceral fats are higher than the normal level is classified into "corpulence". Visceral fats are recognized as a risk factor of lifestyle-related diseases.

The term "hyperlipemia" as referred to as in the present invention means the fettle that triglyceride and/or cholesterol content(s) in the blood and/or body fluid is higher than the normal level. In the case of human, "hyperlipemia" means one whose triglyceride content in blood is higher than 150 mg/100 ml-blood. Also, "hyperlipemia" includes "hypercholesterolemia". The term "hypercholesterolemia" as referred to as in the present invention means the fettle that total cholesterol content in the blood is 220 mg/100 ml-blood or higher. Also, "hypercholesterolemia" includes fettles that the high-density lipoprotein (HDL) cholesterol content in the blood is 41 mg/100 ml-blood or lower and that remnant-like lipoprotein cholesterol content in the blood is 7.5 mg/100 ml-blood or higher.

Since CTS and its saccharide-derivatives, effective ingredients of the lipid-regulating agent of the present invention, are stable and do not affect the flavors of foods and beverages, the lipid-regulating agent of the present invention can be used intact or in combination with one or more ingredients, having an effect on lipid-metabolism in the living body, such as xyloglucan and its hydrolyzates, galactooligosaccharide-sulfate obtainable by hydrolyzing porphylan, hesperetin, naringenin, etc., disclosed in Japanese Patent Kokai Nos. 147,934/95, 224,608/97, 349,485/99, and 280,358/96. Further, the lipid-regulating agent of the present invention can be arbitrarily used freely in combination with dietary fibers such as cellulose, pectin, pullulan, amylose, their derivatives, and hemicellulose, disclosed in "SHOKUMOTSU-SENI KISO-TO-OYO" (Dietary fiber, its basis and application) published by ASAKURA-SHOTEN in 1997. In addition to those ingredients, one or more well-known ingredients which are known to involve the metabolism and the regulation of lipids, such as flavonoids including hesperidin, enzyme-treated hesperidin, naringin, enzyme-treated naringin, rutin, enzyme-treated rutin, and proanthocyanidin; catechins including catechin, epicatechin, and epigallocatechin; plant sterols including diacylglycerol, polyenphosphatidylcholine; royal jelly, flavastatin sodium salt, simbastatin, simfibrate, nicotinic acid, nicomol, clinofibrate, clofibrate, pantethine, riboflavin butyrate, etc., can be arbitrarily used with the lipid-regulating agent of the present invention to enhance the lipid-regulating activity.

The lipid-regulating agent of the present invention, comprising CTS and/or its saccharide-derivatives as effective ingredients, can be arbitrarily used intact or by admixing with fillers, excipients, binders, etc., to shape into various forms such as granules, spheres, sticks, plates, cubes, tablets, etc.

The lipid-regulating agent, comprising CTS and its saccharide-derivatives, of the present invention well harmonizes with various substances having a taste such as sourness, salty taste, astringency, delicious taste, bitterness, etc., and has a satisfactory acid tolerance and thermal stability. Therefore, the lipid-regulating agent can be advantageously used as a material for general foods, medicated cosmetics, pharmaceuticals, feeds, and pet foods. The products comprising the lipid-regulating agent can be used similarly as those not comprising the agent. The products comprising the lipid-regulating agent can be advantageously used as foods and beverages, medicated cosmetics, pharmaceuticals, their intermediates, and materials for patients of lifestyle-related diseases, whose intake of calorie and lipids are restricted, for the purpose of diet, the prevention of lifestyle-related diseases, curing or preventing adiposis, diabetes, hyperlipemia, fatty liver, etc. The lipid-regulating agent of the present invention can be arbitrarily used for feeds, pet foods, etc., for the purpose of preventing adiposis or improving hyperlipemia and fatty liver of domestic animals, poultry, and pets.

The lipid-regulating agent of the present invention can be used for producing various foods and beverages such as seasonings, mixed seasonings, various Japanese or Western confectioneries, breads, ice-creams, syrups, pastes, processed vegetables, pickles, seasoning for pickles, meat products, marine products, delicacy, side dishes, milk products, cooling beverages, various premixes, instant foods, chilled foods, frozen foods, retort foods, dried foods, baby foods, foods for curing, drinks, peptide foods, etc. The lipid-regulating agent of the present invention can be used as a substitute of a part or the whole of fats for producing foods and beverages comprising fat. Foods and beverages with a creamy taste and good texture can be produced by using the lipid-regulating agent of the present invention even in the case of using low amounts of fat. Such foods and beverages comprising fat include brownie, pie filling, frozen dessert, salad dressing, spread, cake, cookie, powdery beverage, etc., which are produced by using lard, beef tallow, fish oil, vegetable oil, milk fat, butter, cheese, shortening, margarine, cooking oil, and cooking fat. Since foods and beverages comprising CTS and saccharide-derivatives of CTS have the lipid-regulating activity, they can be used as compositions for regulating the amount of lipids.

The lipid-regulating agent comprising CTS and/or its saccharide-derivatives can be arbitrarily used for imparting lipid-regulating activity to feeds, baits, pet foods for breeding animals including domestic animals, poultries, honey bee, silkworm, freshwater fish, sea fish, crustacea, etc., by incorporating the agent into them. Further, since CTS and its saccharide-derivatives regulate the functions of the intestines and inhibit the re-absorption of bile acids in the intestine, the lipid-regulating agent can be arbitrarily used for regulating the functions of the intestines and/or regulating the metabolism of bile acids.

The methods for incorporating the lipid-regulating agent of the present invention into objective compositions are not specifically restricted. The agent can be incorporated into the compositions before or after completion of their processing. The methods for incorporating the agent can be arbitrarily selected from the following conventional methods; mixing, kneading, dissolving, melting, dispersing, suspending, emulsifying, penetrating, dispersing, applying, attaching, spraying, coating, injecting, crystallizing, and solidifying. Also, one or more these methods can be arbitrarily combined.

It is preferable that the lipid-regulating agent of the present invention comprises effective ingredients, CTS and/or its saccharide-derivatives, in a total amount of about 0.1 w/w % (hereinafter, "w/w %" is simply abbreviated as "%" in this specification unless specified otherwise) or higher, more preferably, 0.5% or higher, most preferably, 1.0% or higher. CTS and/or its saccharide-derivatives can be used intact or in the form of a saccharide composition further comprising other saccharides such as glucose, isomaltose, maltose, oligosaccharides, dextrins, etc., which are produced during the process of producing CTS and its saccharide-derivatives, as lipid-regulating agent of the present invention as long as it can be used for reducing and/or keeping the amount of lipids in a living body. When the composition comprising the lipid-regulating agent also comprises biologically active substances, having an amino residue in its molecule, such as amino acids as effective ingredients and reducing saccharides including glucose, it is supposed that the effective ingredients are deteriorated by the Maillard reaction and the quality of the composition is also deteriorated. In such cases, it is preferable to use the lipid-regulating agent comprising CTS and/or its saccharide-derivatives in a total amount of 98% or higher, more preferably, 99% or higher, most preferably, 99.5% or higher. Further, a saccharide composition comprising CTS and/or its saccharide-derivatives with a reduced reducibility, which is prepared by hydrogenating other reducing saccharides, can be used as the lipid-regulating agent of the present invention.

Since CTS and its saccharide-derivatives are stable saccharides, they can be optionally incorporated into one or more substances selected from the group consisting of saccharides such as reducing saccharides, non-reducing saccharides except for CTS and its saccharide-derivatives, cyclodextrin, sugar alcohols, water-soluble polysaccharides; polyphenols such as flavonoids and catechins; sweeteners, spices, acidifiers, seasonings, alcohols, fatty acids and their salts, inorganic salts, emulsifiers, flavors, colorings, antioxidants, and substances having a chelating activity, according to the object such as improving the dispersiency or filling, as far as they do not affect the effect and quality of the composition comprising a lipid-regulating agent of the present invention. If necessary, a suitable amount of one or more conventional substances such as preserves, seasonings, sweeteners, stabilizers, alcohols, disinfectants, etc., can be used with CTS and its saccharide-derivatives. The lipid-regulating agents, thus obtained, are not restricted by their forms and any form selected from the group consisting of syrup, paste, massecuite, powder, crystal, granule, and tablet can be arbitrarily used.

The lipid-regulating agent of the present invention can be arbitrarily used after mixed with a suitable amount of one or more saccharides or sweeteners selected from the group consisting of starch hydrolyzate, glucose, maltose, trehalose, sucrose, isomerized sugar, honey, maple sugar, isomaltooligosaccharides, galactooligosaccharides, fructooligosaccharides, nigerooligosaccharides, xylooligosaccharides, agarooligosaccharides, chitooligosaccharides, beet oligosaccharides, saccharide-derivatives of α,α-trehalose such as α-glucosyl α,α-trehalose, α-maltosyl α,α-trehalose, etc., disclosed in Japanese Patent Kokai No. 143,876/95, lactosucrose, sorbitol, maltitol, lactitol, xylitol, erythritol, dihydrochalcone, stevioside, α-glycosylstevioside, rebaudioside, glycyrrhizin, L-aspartyl L-phenylalanine methyl ester, saccharine, glycine, alanine, acesulfame K, and sucralose. The lipid-regulating agent of the present invention can be used after mixed with fillers such as dextrin, starch, lactose, etc.

The requisite intake per day of the lipid-regulating agent of the present invention is not specifically restricted as far as the agent exercises the lipid-regulating activity. It is preferable to take the effective ingredients, CTS and/or its saccharide-derivatives, in total, usually, in an amount of about 0.01 g or higher, more preferably, about 0.5 g or higher, most preferably, about 1.2 g or higher, on a dry solid basis. In the case of taking the agent in an amount of less than 0.01 g per day, the lipid-regulating activity is insufficient. The requisite intake-frequency per day of the lipid-regulating agent of the present invention is not specifically restricted as far as it can be enough to intake the amount of CTS and/or its saccharide-derivatives for exercising the lipid-regulating activity. The agent can be taken the requisite amount per day per ones or several times. The lipid-regulating agent of the present invention may rises diarrhea depending on the constitution when large amount of the agent is taken. Usually, it is preferable to intake the agent by dividing for several times. Particularly, it is preferable to use the agent as a material of diet meal or to intake the agent before or after taking meal. It is preferable to take the lipid-regulating agent orally intact or in the form of a composition such as foods and beverages, pharmaceuticals, and medicated cosmetics. In the case of being impossible to intake orally, the agent can be arbitrarily injected into stomach or intestines directly by using a catheter or the like.

The following experiments explain a lipid-regulating agent using CTS or the mixture of CTS and its saccharide-derivative(s) in detail.

Experiment 1

As disclosed in International Publication No. WO 01/090, 338, it is known that CTS has a dietary fiber-like activity. Therefore, the present inventors considered that CTS may have some effects on living bodies. They investigated the effect of CTS on the lipid metabolism using rats by administrating a feed comprising a representative dietary fiber, cellulose or non-fiber feed as controls.

Experiment 1-1

Feeding Test on Rat and the Measurement of the Weight

Fifty 5-weeks aged male Wister-rats, having a weight of 110 to 120 grams, commercialized by Charles River Japan, Kanagawa, Japan, were fed on a non-fiber feed having a composition shown in Table 1 for one week for habituation. After the habituation, the rats were randomly divided into five groups and each group was fed on either of feeds shown in Table 1, i.e., a non-fiber feed, a feed in which cellulose was incorporated into the non-fiber feed to give a content of 5% (hereinafter, abbreviated as "fiber feed"), a feed in which powdery anhydrous crystalline CTS (purity of CTS: 99.5%), prepared by the method of Example A-3 described later, was incorporated into the non-fiber feed to give a content of 1, 2, or 5%, on a dry solid basis, and the feeding test was carried out for four weeks. A fiber-feed and three kinds of feeds comprising CTS were prepared to give the total content of cellulose or CTS and corn starch of 44.75% to the total weight of each feed. The rats were kept under the conditions of keeping the temperature at 25° C., lighting and shading for 12 hours each/day, and allowing the rats to eat the respective feed and water freely. After the completion of the feeding test, weight of individuals in each group was measured and an average weight and an average increase of weight of each group during the test period were calculated. The results are in Table 2. Also, the total amount of feed fed to individual rat in each group during the 4-weeks test period and an average amount of CTS taken per day per kg-weight-rat were calculated and the results are in Table 2.

Determination of the Amount of Lipids in Blood Plasma

After the feeding test, each rat was fasted for one day and incised under anesthesia with ether. Then, blood was collected from the main vein of each rat using a syringe treated with 1% EDTA. Each collected blood was centrifuged at 3,500 rpm for 10 minutes to separate blood plasma and the contents of total cholesterol, triglyceride, and phospholipids in the resulting blood plasma were measured by using kits, "CHOLESTEROL C-TEST-WAKO", "TRIGLYCERIDE-TEST-WAKO", and "PHOSPHOLIPID C-TEST-WAKO", respectively, commercialized by Wako Pure Chemical Industries, Ltd., Osaka, Japan. In order to check the hepatic function disorder, GOT activity in the blood plasma was measured using a kit, "GOT-TEST-WAKO", commercialized by Wako Pure Chemical Industries, Ltd., Osaka, Japan. The content of LDL-cholesterol was calculated by subtracting the content of HDL-cholesterol from the total content of cholesterol. The results are in Table 3. A significant difference test was done with respect to the group fed on fiber feed. In the case of cholesterol, a significant difference test was done with respect to the group fed on non-fiber feed because it was believed that cellulose has no activity of reducing the amount of cholesterol by oral intake as described in "*SHOKUMOTSU-SENI KISO-TO-OYO* (Dietary fiber, its basis and application)" published by ASAKURA-SHOTEN in 1997.

Determination of the Amount of Lipids in Organs and Tissues

After collecting the blood described above, each rat was killed by dislocating its cervical vertebrae and anatomized. Then, adipose tissues surrounding intestinal membrane, kidney, and testis, as well as liver and cecum, were collected. The wet-weight of those adipose tissues was measured and the results are in Table 4. In the case of liver, the wet-weight and the amount of total lipid, total cholesterol, triglyceride, and phospholipids were measured and the results are in Table 5. The amount of total lipid, total cholesterol, triglyceride, and phospholipids in the liver were measured by the steps of homogenizing four parts by weight of liver with four parts by weight of water using a homogenizer; extracting lipid by repeating three-times the following procedure of adding eight milliliters of a chloroform-methanol (2:1, by volume) solution, stirring the mixture, and centrifuging (3,000 rpm, 15 min) to collect chloroform phase; concentrating the resulting chloroform solution; and measuring those according to the same procedure used in the case of lipids in blood plasma.

Measurement of the Cecal Content and Determination of the Amount of Bile Acids in Cecal Content Just after extirpating cecum as described above, its content was collected and weighted. The concentration of bile acids was measured by the steps of adding two milliliters of 80% (v/v) methanol aqueous solution to 0.2 gram of the cecal content, extracting bile acids at 70° C. for 30 min, centrifuging (3,500 rpm, 10 min) the mixture, drying the resulting supernatant in a dessicator with $P_2O_5$ for overnight, and measuring bile acids using a kit, "BILE ACID-TEST WAKO", commercialized by Wako Pure Chemical Industries, Ltd., Osaka, Japan. The amount of bile acids was calculated by multiplying the concentration of bile acids and weight of the cecal content. The results are in Table 6. The weight of cecal tissue was calculated by subtracting the wet-weight of cecal content from the total wet-weight of extirpated cecum.

TABLE 1

| | Feed | | | | |
|---|---|---|---|---|---|
| Ingredient | Non-fiber | Fiber | 1% (w/w) * CTS | 2% (w/w) * CTS | 5% (w/w) * CTS |
| CTS | 0 | 0 | 1.0 | 2.0 | 5.0 |
| Cellulose | 0 | 5.0 | 0 | 0 | 0 |
| Corn starch | 44.75 | 39.75 | 43.75 | 42.75 | 39.75 |
| α-Starch | 13.20 | 13.20 | 13.20 | 13.20 | 13.20 |
| Casein | 20.00 | 20.00 | 20.00 | 20.00 | 20.00 |
| Sucrose | 10.00 | 10.00 | 10.00 | 10.00 | 10.00 |
| Soybean oil | 7.00 | 7.00 | 7.00 | 7.00 | 7.00 |
| Mineral mix | 3.50 | 3.50 | 3.50 | 3.50 | 3.50 |
| Vitamin mix | 1.00 | 1.00 | 1.00 | 1.00 | 1.00 |
| D,L-Methionine | 0.30 | 0.30 | 0.30 | 0.30 | 0.30 |
| Choline bitartrate | 0.25 | 0.25 | 0.25 | 0.25 | 0.25 |
| t-Butyl hydroquinone | 0.0014 | 0.0014 | 0.0014 | 0.0014 | 0.0014 |

* on a dry solid basis

TABLE 2

| | Feed | | | | |
|---|---|---|---|---|---|
| Measurement items** | Non-fiber | Fiber | 1% (w/w) CTS | 2% (w/w) CTS | 5% (w/w) CTS |
| Weight (g/individual) | 342 | 345 | 337 | 342 | 322* |
| Increase of weight (g/individual/28 days) | 168 | 171 | 164 | 169 | 149* |
| Total amount of feed taken (g/individual/28 days) | 575 | 580 | 593 | 601 | 561 |
| The amount of CTS taken per weight per day (g/kg/day) | 0 | 0 | 0.63 | 1.25 | 3.1 |

*differ significantly (p < 0.05)
**Significant difference is evaluated with respect to the group fed on feed comprising fiber.

TABLE 3

| Measurement items** | Feed | | | | |
|---|---|---|---|---|---|
| | Non-fiber | Fiber | 1% (w/w) CTS | 2% (w/w) CTS | 5% (w/w) CTS |
| Total cholesterols (mg/dl) | 69.8 | 64.1 | 67.1 | 66.1 | 59.4* |
| Triglycerides (mg/dl) | 41.0 | 48.2 | 44.2 | 28.7* | 21.7* |
| Phospholipids (mg/dl) | 125 | 115 | 116 | 115 | 107 |
| GOT (IU) | 10.5 | 10.1 | 10.3 | 10.2 | 10.7 |

*differ significantly ($p < 0.05$)
**In the case of cholesterol, significant difference is evaluated with respect to the group fed on non-fiber feed. In other cases, significant difference is evaluated with respect to the group fed on feed comprising fiber.

TABLE 4

| Measurement items** | Feed | | | | |
|---|---|---|---|---|---|
| | Non-fiber | Fiber | 1% (w/w) CTS | 2% (w/w) CTS | 5% (w/w) CTS |
| Adipose surrounding intestinal membrane (g/individual) | 4.4 | 4.3 | 3.7 | 3.1* | 1.9* |
| Adipose surrounding kidney (g/individual) | 5.3 | 4.8 | 3.7* | 2.9* | 2.1* |
| Adipose surrounding testis (g/individual) | 5.3 | 5.3 | 4.0* | 3.9* | 3.1* |

*differ significantly ($p < 0.05$)
**Significant difference is evaluated with respect to the group fed on a feed comprising fiber.

TABLE 5

| Measurement items** | Feed | | | | |
|---|---|---|---|---|---|
| | Non-fiber | Fiber | 1% (w/w) CTS | 2% (w/w) CTS | 5% (w/w) CTS |
| Weight of liver (g/individual) | 8.8 | 8.7 | 8.4 | 8.6 | 8.1 |
| Total lipids in liver (mg/individual) | 645 | 586 | 510 | 598 | 575 |
| Total cholesterols in liver (mg/individual) | 39.5 | 36.8 | 35.9 | 37.2 | 35.4 |
| Triglycerides in liver (mg/individual) | 329 | 265 | 186 | 254 | 239 |
| Phospholipids in liver (mg/individual) | 154 | 139 | 140 | 149 | 142 |

*differ significantly ($p < 0.05$)
**In the case of cholesterol, significant difference is evaluated with respect to the group fed on a non-fiber feed. In other cases, significant difference is evaluated with respect to the group fed on feed comprising fiber.

TABLE 6

| Measurement items** | Feed | | | | |
|---|---|---|---|---|---|
| | Non-fiber | Fiber | 1% (w/w) CTS | 2% (w/w) CTS | 5% (w/w) CTS |
| Weight of cecal tissue (g/individual) | 0.85 | 0.87 | 1.12* | 1.19* | 1.39* |
| Weight of cecal content (g/individual) | 2.1 | 2.5 | 2.4 | 3.0* | 3.5* |
| Bile acids in cecum (μmol) | 0.91 | 0.82 | 1.15* | 1.36* | 1.53* |

*differ significantly ($p < 0.05$)
**Significant difference is evaluated with respect to the group fed on the fiber-feed.

Effects of the Administration of CTS on the Weight of Rat and the Amount of Feed Intake As evident from Table 2, in the case of the group fed on the feed comprising 5% CTS, significant difference of the weight and the inhibition of weight increase were observed in comparison with a group fed on the fiber-feed. No significant difference was observed in the total amount of feed intake among any group during the test period.

Effect of the Administration of CTS on the Amount of Lipids

As evident from Table 3, as regards the amount of lipids in the blood plasma, total amount of cholesterol in the group fed on a feed comprising 5% CTS is significantly lower than that in the group fed on non-fiber feed. The amounts of triglyceride in the groups fed on feeds comprising 2% and 5% CTS were significantly lower than that in the group fed on a fiber-feed. Significant differences were not observed in the amount of phospholipids and GOT activity among any groups. As evident from Table 4, the accumulation of lipids around intestine, kidney, and testis in the groups fed on feeds comprising 2% and 5% CTS was significantly lower than those in the group fed on a fiber-feed. Also, the accumulation of lipids around kidney and testis in the group fed on a feed comprising 1% CTS was significantly lower than those in the group fed on a fiber-feed. As evident from Table 5, the amounts of triglyceride in liver in the groups fed on feeds comprising CTS were slightly lower than those in the groups fed on a non-fiber feed or a fiber-feed, but no significant difference was observed because of varying individual values. No significant difference was observed in other lipids.

Effects of the Administration of CTS on the Weight of Cecal Contents and the Amount of Bile Acids in Cecum As evident from Table 6, the weight of cecal tissue and the amount of cecal content and that of bile acids in cecum in the groups fed on feeds comprising 2% and 5% CTS were significantly higher than those in the group fed on a fiber-feed. Also, the weight of cecal tissue and the amount of bile acids in cecum in the group fed on a feed comprising 1% CTS were significantly higher than those in the group fed on a fiber-feed.

From those results, it was revealed that CTS has an effect of regulating the amount of lipids such as triglycerides in blood plasma and lipids around organs (visceral lipids), and those effects are very stronger than those of cellulose which is a representative dietary fiber. Particularly, since CTS showed significant lipid-regulating effects on triglyceride in blood plasma and perivisceral lipids and tend to lower triglyceride in liver, the lipid-lowering effect in serum is not caused by the mechanism of accumulating triglyceride in adipose tissue and but by lowering lipids in the living body in rats fed on CTS. The effect of regulating the amount of lipids, i.e., the effect of lowering the amount of lipids in the living body depends on the intake amount of CTS. Varying with the kinds of lipids, the effects of lowering the amount of lipids was observed even in the case of using a feed with a CTS content of 1% (the average intake of CTS per day was 0.63 g per individual). It was confirmed that a remarkable lipid-regulating effect was observed in the case of using feeds with a CTS content of 2% or higher (the average intake of CTS per day was 1.25 g or higher per individual). Further, the effect of lowering the amount of cholesterols was observed in the case of rats fed on a feed with CTS content of 5%. It is believed that the effect is not observed in cellulose. Since the amount of bile acids involving the absorption of lipids was increased in intestinal cecum, CTS has a potential of inhibiting the re-absorption of bile acids and the absorption of lipids by small intestine. It is suggested that one of the mechanism of regulating the amount of lipids by CTS is the inhibition of the re-absorption of bile acids by small intestine.

GOT values, which are markers of functional disorder of liver, of rats were not significantly changed during the test period regardless of the intake of CTS. These results indicate that the lipid-regulating activity of CTS is caused by disorder of liver. Although the concrete data are not shown, two individuals in ten individuals of rats, fed on a feed with CTS content of 5%, showed a symptom of diarrhea for 2-3 days after initial intake of CTS and then cured. This result indicates that CTS is a hardly digestible saccharide, and these coincidents with the results disclosed in International Publication No. WO 01/090,338 by the same applicant as the present invention. The symptom of diarrhea was not observed in rats fed on a feed with CTS content of 2%. The result of curing the symptom of diarrhea indicates that intestinal bacteria of rats adjust with CTS gradually.

Experiment 1-2

Effect of the Administration of a Saccharide Comprising CTS and its Saccharide-Derivatives on the Lipids of Rat From the results in Experiment 1-1, it was confirmed that CTS has a lipid-regulating activity for rat. Successively, a test was carried out to confirm that a saccharide comprising CTS and its saccharide-derivatives has the same activity as in the case of CTS only as follows. Further, the amount of bile acids which are known to involve the lipid-regulation and GOT activity which is used as an index of hepatic function disorder were measured. The amount of LDL-cholesterol was measured along with the amount of total cholesterol to investigate that the decline of the amount of cholesterol observed in Experiment 1-1 is caused by decreasing the amount of LDL-cholesterol, which is recognized as a cause of arterial sclerosis and cardiac infarction, or not. A significant difference test was done with respect to the group fed on the fiber feed. In the case of cholesterol, significant difference test was done with respect to the group fed on the non-fiber feed.

Feeding Test on Rat and Measurement of the Weight

An experiment for investigating the effects of the administration of a saccharide comprising CTS and its saccharide-derivatives on the amount of lipids of rat was carried out as follows:

Fifty 5-weeks aged male Wister-rats, having a weight of 110 to 120 grams, commercialized by Charles River Japan, Kanagawa, Japan, were fed on a non-fiber feed having a composition shown in Table 7 for one week for habituation. After the habituation, the rats were randomly divided 10 individuals each into five groups and each group was fed on either of feeds shown in Table 7, i.e., a non-fiber feed, a fiber feed, a feed in which powdery product, prepared by spray-drying a syrup comprising 35.2%, on a dry solid basis, of CTS and 15.6%, on a dry solid basis of its saccharide-derivatives by the method of Example A-2 described after, was incorporated into the non-fiber feed to give a total content of CTS and its saccharide-derivative of 1, 2, or 5%, on a dry solid basis, and the feeding test was carried out for four weeks. A fiber-feed and three kinds of feed comprising a saccharide comprising CTS and its saccharide-derivatives were prepared to give the total content of cellulose or a saccharide, comprising CTS and its saccharide-derivatives, and corn starch of 44.75% to the total weight of the feed. After the completion of the feeding test, weight of individuals in each group was measured and calculated an average weight of a group and an average increase of weight in the test period. The results are in Table 8. Also, the total amount of feed fed to individual rat in each group during the 4-weeks test period and an average amount of CTS or the total of CTS and its saccharide-derivatives intakened per day per kg-weight-rat were calculated and are in Table 8.

Determination of the Amount of Lipids in Blood Plasma

After the feeding test, the contents of total cholesterol, HDL-cholesterol, triglyceride, and phospholipids and GOT activity in the blood plasma were measured according to the methods described in Experiment 1-1. The content of LDL-cholesterol was calculated by subtracting the content of HDL-cholesterol from the total content of cholesterol. The content of HDL-cholesterol was measured using a kit, "HDL-CHOLESTEROL-TEST-WAKO", commercialized by Wako Pure Chemical Industries, Ltd., Osaka, Japan. The results are in Table 9.

Determination of the Amount of Lipids in Organs or Tissues

After collecting the blood described above, the wet-weights of adipose tissues surrounding intestinal membrane, kidney, and testis were measured according to the method described in Experiment 1-1 and the results are in Table 10. The wet-weight of liver and the amount of total lipids, total cholesterol, triglycerides, and phospholipids in the liver were measured and the results are in Table 11.

Measurement of Weight of Cecal Contents and the Determination of the Amount of Bale Acid in Cecum Just after extirpating cecum as described above, its content was collected and the weight of cecal content and the amount of bile acids were measured according to the methods described in Experiment 1-1. The results are in Table 12.

TABLE 7

| | Feed | | | | |
|---|---|---|---|---|---|
| Ingredient | Non-fiber | Fiber | 1% (w/w)* CTS + SDCTS** | 2% (w/w)* CTS + SDCTS** | 5% (w/w)* CTS + SDCTS** |
| Powdery composition comprising CTS and SDCTS** | 0 | 0 | 1.97 | 3.94 | 9.84 |
| Cellulose | 0 | 5 | 0 | 0 | 0 |
| Corn starch | 44.75 | 39.75 | 42.78 | 40.81 | 34.91 |
| α-Starch | 13.20 | 13.20 | 13.20 | 13.20 | 13.20 |
| Casein | 20.00 | 20.00 | 20.00 | 20.00 | 20.00 |
| Sucrose | 10.00 | 10.00 | 10.00 | 10.00 | 10.00 |
| Soybean oil | 7.00 | 7.00 | 7.00 | 7.00 | 7.00 |
| Mineral mix | 3.50 | 3.50 | 3.50 | 3.50 | 3.50 |
| Vitamin mix | 1.00 | 1.00 | 1.00 | 1.00 | 1.00 |
| D,L-Methionine | 0.30 | 0.30 | 0.30 | 0.30 | 0.30 |
| Choline bitartrate | 0.25 | 0.25 | 0.25 | 0.25 | 0.25 |
| t-Butyl hydroquinone | 0.0014 | 0.0014 | 0.0014 | 0.0014 | 0.0014 |

*on a dry solid basis
**Saccharide-derivative of CTS

TABLE 8

| | Feed | | | | |
|---|---|---|---|---|---|
| Measurement items** | Non-fiber | Fiber | 1% (w/w) CTS + SDCTS | 2% (w/w) CTS + SDCTS | 5% (w/w) CTS + SDCTS |
| Weight (g/individual) | 371 | 349 | 359 | 356 | 351* |
| Increase of weight (g/individual/28 days) | 205 | 182 | 192 | 189 | 185* |
| Total amount of feed taken (g/individual/28 days) | 584 | 580 | 583 | 588 | 586 |
| The total amount of CTS and SDCTS taken per weight per day (g/kg/day) | 0 | 0 | 0.58 (0.38)*** | 1.18 (0.81)*** | 2.98 (2.05)*** |

*differ significantly (p < 0.05)
**Significant difference is evaluated with respect to the group fed on the fiber-feed.
***The amount of CTS only

TABLE 9

| | Feed | | | | |
|---|---|---|---|---|---|
| Measurement items** | Non-fiber | Fiber | 1% (w/w) CTS + SDCTS | 2% (w/w) CTS + SDCTS | 5% (w/w) CTS + SDCTS |
| Total cholesterol (mg/dl) | 58.9 | 55.3 | 45.7* | 49.4* | 44.5* |
| HDL-cholesterol (mg/dl) | 32.8 | 32.0 | 24.8* | 29.8 | 26.2* |

TABLE 9-continued

| Measurement items** | Feed | | | | |
|---|---|---|---|---|---|
| | Non-fiber | Fiber | 1% (w/w) CTS + SDCTS | 2% (w/w) CTS + SDCTS | 5% (w/w) CTS + SDCTS |
| LDL-cholesterol (mg/dl) | 26.1 | 23.3 | 20.9* | 19.6* | 18.3* |
| Percentage of LDL-cholesterol to total cholesterol (%) | 44.1 | 42.3 | 46.4 | 40.1 | 41.2 |
| Triglycerides (mg/dl) | 94.2 | 72.9 | 65.0 | 53.8 | 32.5* |
| Phospholipids (mg/dl) | 108.7 | 98.2 | 85.6* | 90.7 | 83.9* |
| GOT (IU) | 9.3 | 10.7 | 11.2 | 11.1 | 8.6* |

*differ significantly ($p < 0.05$)
**In the case of cholesterol, significant difference is evaluated with respect to the group fed on the non-fiber feed. In other cases, significant difference is evaluated with respect to the group fed on the fiber-feed.

TABLE 10

| Measurement items** | Feed | | | | |
|---|---|---|---|---|---|
| | Non-fiber | Fiber | 1% (w/w) CTS + SDCTS | 2% (w/w) CTS + SDCTS | 5% (w/w) CTS + SDCTS |
| Adipose surrounding intestinal membrane (g/individual) | 5.8 | 5.7 | 5.4 | 4.2* | 3.9* |
| Adipose surrounding kidney (g/individual) | 7.4 | 6.9 | 5.5 | 4.4* | 3.8* |
| Adipose surrounding testis (g/individual) | 8.0 | 6.6 | 5.8 | 4.9* | 4.8* |

*differ significantly ($p < 0.05$)
**Significant difference is evaluated with respect to the group fed on the fiber-feed.

TABLE 11

| Measurement items** | Feed | | | | |
|---|---|---|---|---|---|
| | Non-fiber | Fiber | 1% (w/w) CTS + SDCTS | 2% (w/w) CTS + SDCTS | 5% (w/w) CTS + SDCTS |
| Weight of liver (g/individual) | 9.8 | 9.1 | 9.0 | 9.0 | 8.7 |
| Total lipids in liver (mg/individual) | 623 | 653 | 605 | 598 | 550* |
| Total cholesterols in liver (mg/individual) | 38.3 | 43.4* | 43.3* | 39.3 | 38.0 |
| Triglycerides in liver (mg/individual) | 266 | 292 | 256 | 239* | 220* |
| Phospholipids in liver (mg/individual) | 153 | 165 | 176 | 169 | 153 |

*differ significantly ($p < 0.05$)
**In the case of cholesterol, significant difference is evaluated with respect to the group fed on the non-fiber feed. In other cases, significant difference is evaluated with respect to the group fed on the fiber feed.

TABLE 12

| Measurement items** | Feed | | | | |
|---|---|---|---|---|---|
| | Non-fiber | Fiber | 1% (w/w) CTS + SDCTS | 2% (w/w) CTS + SDCTS | 5% (w/w) CTS + SDCTS |
| Weight of cecal content (g/individual) | 2.23 | 2.38 | 2.63 | 2.97* | 4.32* |

TABLE 12-continued

| Measurement items** | Feed | | | | |
|---|---|---|---|---|---|
| | Non-fiber | Fiber | 1% (w/w) CTS + SDCTS | 2% (w/w) CTS + SDCTS | 5% (w/w) CTS + SDCTS |
| Bile acids in cecal content (μmol/individual) | 14.3 | 16.1 | 23.8* | 25.0* | 35.4* |

*differ significantly (p < 0.05)
**Significant difference is evaluated with respect to the group fed on the fiber-feed.

Effects of the Administration of CTS and its Saccharide-Derivatives on the Weight of Rat and the Amount of Feed Intake As evident from Table 8, significant differences on the weight and the amount of feed taken were not observed among any groups.

Effect of the Administration of CTS and its Saccharide-Derivative on the Amount of Lipids in Blood Plasma As evident from Table 9, the amounts of total cholesterol and LDL-cholesterol in blood plasma in the groups fed on a feed comprising 1, 2, or 5%, on a dry solid basis, of CTS were significantly lower than those in the group fed on non-fiber feed. Further, the ratio of the amount of LDL-cholesterol to the amount of total cholesterol in blood plasma is not significantly changed in any groups. The amount of triglyceride in blood plasma was lowered depending on the contents of CTS and its saccharide-derivatives in the feed. That in the group fed on the feed comprising CTS and its saccharide-derivatives of 5%, on a dry solid basis, was significantly lower than that in the group fed on the fiber-feed. The amounts of phospholipids in the groups fed on the feed CTS and its saccharide-derivatives of 1 or 5%, on a dry solid basis, were significantly lower than that in the group fed on the fiber-feed.

Effect of the Administration of CTS and its Saccharide-Derivative on the Amount of Lipids in Tissues As evident from Table 10, the accumulation of lipids around intestinal membrane, kidney, and testis was inhibited depending on the content of CTS and its saccharide-derivatives in the group fed on the feed comprising CTS and its saccharide-derivatives. The accumulation of lipids in the group fed on the feed comprising CTS and its saccharide-derivatives of 2 or 5%, on a dry solid basis, were significantly lower than that in the group fed on the fiber-feed. As evident from Table 11, as regard to the liver, the total amount of lipids and the amount of triglycerides were lowered depending on the content of CTS and its saccharide-derivatives in the group fed on the feed comprising CTS and its saccharide-derivatives. The total amount of lipids in the liver in the group fed on the feed comprising CTS and its saccharide-derivative of 5%, on a dry solid basis, was significantly lower than that in the group fed on the fiber-feed. The amounts of triglycerides in the liver in the groups fed on the feed comprising CTS and its saccharide-derivative of 2 or 5%, on a dry solid basis, were significantly lower than that in the group fed on the fiber-feed. The amounts of total cholesterol in the liver in the groups fed on the feed comprising CTS and its saccharide-derivative of 1%, on a dry solid basis, were significantly higher than that in the group fed on the non-fiber feed. The weight of liver and the amount of phospholipids were not significantly different among any groups.

Effects of the Administration of CTS and its a Saccharide-Derivative on the Weight of Cecal Contents and the Amount of Bile Acids in Cecum As evident from Table 12, the amount of cecal content and that of bile acids in cecum were increased depending on the total amount, on a dry solid basis, of CTS and its saccharide-derivatives in the groups fed on feeds comprising CTS and its saccharide-derivatives. The amount of cecal contents in the groups fed on feeds comprising 2% and 5% of CTS and its saccharide-derivatives were significantly higher than that in the group fed on a fiber-feed. The amount of bile acids in cecum in any group fed on a feed comprising CTS and its saccharide-derivatives were significantly higher than that in the group fed on a fiber-feed.

These results indicate that saccharides comprising CTS and its saccharide-derivatives also have the lipid-regulating effect as in the case of CTS. It was confirmed that the effects of regulating the amount of lipids depend on the total amount of CTS and its saccharide-derivatives taken. Varying with the kinds of lipids, the effects of lowering the amount of lipids was observed even in the case of using a feed with a total content of CTS and its saccharide-derivatives of 1%, on a dry solid basis (the average intake of CTS per day was 0.56 g per individual). It was confirmed that a remarkable lipid-regulating effect was observed in the case of using feeds with a total content of CTS and its saccharide-derivatives of 2% or higher, on a dry solid basis (the average intake of CTS per day was 1.18 g or higher per individual). Since the amount of bile acids was increased in intestinal cecum as in the case of using CTS only, it is suggested that both CTS and its saccharide-derivatives have a potential of inhibiting the re-absorption of bile acids and the absorption of lipids by small intestine. In comparison with the feed comprising CTS only, used in Experiment 1-1, a relative CTS content of the feed comprising CTS and its saccharide-derivatives, used in Experiment 1-2, is about 70%. However, almost equivalent lipid-regulating effects are observed in the both Experiments. This result indicates that saccharide-derivatives of CTS have the lipid-regulating activity as in the case of CTS. Although GOT values of rats significantly decreased depending on the amount of intake of CTS in rats fed on the feed comprising CTS and its saccharide-derivatives, the degree of the variation was small. Therefore, it is not believed that these rats develop the disorder of liver.

From the experimental results described above, it is revealed that a composition comprising CTS and/or its saccharide-derivatives can be used for regulating the amount of lipids in a living body.

The following concretely explains a lipid-regulating agent, comprising CTS and/or its saccharide-derivative(s) as an effective ingredients, of the present invention in Examples A; and a composition, comprising the lipid-regulating agent, of the present invention in Examples B. However, the present invention is not restricted by them.

EXAMPLES A

Lipid-Regulating Agent Comprising CTS and/or its Saccharide-Derivartive(s) as an Effective Ingredient(s)

Example A-1

According to the method of Example A-2 disclosed in International Publication No. WO 02/010,361, a lipid-regulating agent in a syrupy form with a concentration of 80%, containing, on a dry solid basis, 0.6% glucose, 1.5% isomaltose, 12.3% maltose, 63.5% CTS, 5.2% saccharide-derivatives of CTS where one or more glucose molecules were bound to CTS, and 16.9% other saccharides, was prepared from potato starch. The product can be advantageously used intact or for preparing a composition such as foods and beverages, medicated cosmetics, pharmaceuticals, feeds, pet-foods, etc., for regulating the amount of lipids by incorporating it into materials such as edible materials and pharmaceutical materials, or intermediate products.

Example A-2

According to the method of Example A-9 disclosed in International Publication No. WO 02/010,361 (except for treatments by α-glucosidase and glucoamylase), a lipid-regulating agent in a syrupy form with a concentration of 73%, containing, on a dry solid basis, 4.1% glucose, 8.1% disaccharides including maltose and isomaltose, 4.6% trisaccharides including maltotriose, 35.2% CTS, 15.6% saccharide-derivatives of CTS where one or more glucose molecules were bound to CTS, and 32.4% other saccharides, was prepared from corn starch. The product can be advantageously used intact or for preparing a composition such as foods and beverages, medicated cosmetics, pharmaceuticals, feeds, pet-foods, etc., for regulating the amount of lipids by incorporating it into materials such as edible materials and pharmaceutical materials, or intermediate products.

Example A-3

A syrup comprising CTS, prepared from corn starch according to the method of Example A-4 disclosed in International Publication No. WO 02/010,361, was purified, concentrated, died, and crystallized according to the method of Example A-6 also disclosed in the above International Publication to produce a powdery lipid-regulating agent, crystalline CTS pentahydrate preparation having a CTS purity of 99.6%. The product can be advantageously used intact or for preparing a composition such as foods and beverages, medicated cosmetics, pharmaceuticals, feeds, pet-foods, etc., for regulating the amount of lipids by incorporating it into materials such as edible materials and pharmaceutical materials, or intermediate products.

The above crystalline CTS pentahydrate preparation was dried according to the method of Experiment 31 and 32 to produce two kinds of lipid-regulating agent, powdery crystalline CTS monohydrate and powdery anhydrous crystalline CTS, respectively. Both lipid-regulating agents can be advantageously used intact or for preparing a composition such as foods and beverages, medicated cosmetics, pharmaceuticals, feeds, pet-foods, etc., for regulating the amount of lipids by incorporating it into materials such as edible materials and pharmaceutical materials, or intermediate products.

Example A-4

Forty parts by weight of "MABIT", anhydrous crystalline maltitol commercialized by Hayashibara Shoji Inc, Okayama, Japan, was admixed with 60 parts by weight of crystalline CTS pentahydrate, obtained in Example A-3, to make into a powdery lipid-regulating agent. The product can be advantageously used intact or for preparing a composition such as foods and beverages, medicated cosmetics, pharmaceuticals, feeds, pet-foods, etc., for regulating the amount of lipids by incorporating it into materials such as edible materials and pharmaceutical materials, or intermediate products.

Example A-5

Fifty parts by weight of "TREHA®", α,α-trehalose commercialized by Hayashibara Shoji Inc, Okayama, Japan, was admixed with 50 parts by weight of crystalline CTS pentahydrate, obtained in Example A-3, to make into a powdery lipid-regulating agent. The product can be advantageously used intact or for preparing a composition such as foods and beverages, medicated cosmetics, pharmaceuticals, feeds, pet-foods, etc., for regulating the amount of lipids by incorporating it into materials such as edible materials and pharmaceutical materials, or intermediate products. Further, the product can be easily used, intact or after incorporating with a sugar ester and the like, in the forms of granule or tablets by granulating or making into tablet.

Example A-6

"TREHA®", a food-grade hydrous crystalline α,α-trehalose commercialized by Hayashibara Shoji Inc., Okayama, Japan, was dissolved in water and the resulting solution was concentrated under reduced pressure with heating to 60° C. to prepare a solution having a α,α-trehalose concentration of 75%. A powdery hydrous crystalline α,α-trehalose, having a α,α-trehalose purity of 99.8%, was prepared from the solution by the steps of crystallizing α,α-trehalose by cooling the solution to the ambient temperature, washing the resulting crystal twice with water, drying the resulting crystal, and pulverizing the dried crystal. Fifty parts by weight of the powdery hydrous crystalline α,α-trehalose and 50 parts by weight of crystalline CTS pentahydrate were mixed to homogeneity to make into a powdery lipid-regulating agent. The product can be advantageously used intact or for preparing a composition such as foods and beverages, medicated cosmetics, pharmaceuticals, feeds, pet-foods, etc., for regulating the amount of lipids by incorporating it into materials such as edible materials and pharmaceutical materials, or intermediate products. Since the product was composed by CTS and α,α-trehalose with high purities, it has a low reactivity and high stability. Therefore, the product can be preferably used to produce a composition, comprising an amino-compound(s) which causes the Maillard reaction with reducing sugars and having a fear of quality deterioration. Further, the product can be easily used, intact or after incorporating with a sugar ester and the like, in the forms of granule or tablets by granulating or making into tablet.

Example A-7

Two parts by weight of ascorbic acid, one part by weight of vitamin E, and 0.5 part by weight of glycerin-fatty acid ester were admixed with 70 parts by weight of a syrup, comprising the mixture of CTS and its saccharide-derivatives, obtained in Example A-1. The product can be advantageously used intact or for preparing a composition such as foods and beverages, medicated cosmetics, pharmaceuticals, feeds, pet-foods, etc., for regulating the amount of lipids by incorporating it into materials such as edible materials and pharmaceutical materials, or intermediate products.

Example A-8

Two parts by weight of ascorbic acid 2-glucoside commercialized by Hayashibara Biochemical Laboratories Inc., Okayama, Japan, and two parts by weight of "αG-RUTIN", an enzymatically modified rutin commercialized by Toyo Sugar Refining Co; ltd., Tokyo, Japan, were admixed with 70 parts by weight of crystalline CTS pentahydrate, obtained in Example A-3 to produce a powdery mixture. The product can be advantageously used intact or for preparing a composition such as foods and beverages, medicated cosmetics, pharmaceuticals, feeds, pet-foods, etc., for regulating the amount of lipids by incorporating it into materials such as edible materials and pharmaceutical materials, or intermediate products.

EXAMPLE B

Composition for Regulating the Amount of Lipids Comprising a Lipid-Regulating Agent which Comprises CTS and/or its Saccharide-Derivative(s) as an Effective Ingredient(s)

Example B-1

Table Sugar for Regulating the Amount of Lipids

Fifty parts by weight of a powdery lipid-regulating agent, crystalline CTS pentahydrate prepared by the method of Example A-3, 46 parts by weight of anhydrous crystalline maltitol, three parts by weight of "αG-HESPERIDIN", glucosyl-hesperidin commercialized by Toyo Sugar Refining Co; ltd., Tokyo, Japan, one part by weight of sucralose commercialized by San-Ei Gen F.F.I., Inc., Osaka, Japan, were dissolved into 200 parts by weight of water and then the mixture was spray-dried by the conventional method to make into powdery sweetener for regulating the amount of lipids. Since CTS and glucosyl-hesperidin regulates the amount of lipids in the living body, the product can be preferably used as a table sugar for the purpose of diet, preventing lifestyle-related disease, or for patients of lifestyle-related disease such as adiposis and hypertension, requiring the restriction of lipids intake.

Example B-2

Sweetener for Regulating the Amount of Lipids

Five parts by weight of powdery lipid-regulating agent, crystalline CTS monohydrate prepared in Example A-3, 94.5 parts by weight of "MABIT®", powdery anhydrous crystalline maltitol commercialized by Hayashibara Shoji Inc., Okayama, Japan, and 0.5 part by weight of "ASPERTAME", L-aspartyl-L-phenylalanine-methyl-ester commercialized by Ajinomoto Co., Inc., Tokyo, Japan, were mixed to homogeneity and granulated by the conventional method to make into granule sweetener for regulating the amount of lipids. CTS in the product regulates lipids in the living body and the product has a lower calorie than sucrose. Since one can keep off calorie by taking the product, the product can be preferably used as a sweetener for the purpose of diet, preventing lifestyle-related disease, or for patients of lifestyle-related disease such as adiposis and hyperlipemia, requiring the restriction of intake of sugars and lipids. Further, the product can be used as a sweetener for pharmaceuticals.

Example B-3

Powdery Fat for Regulating the Amount of Lipids

One hundred parts by weight of soybean salad oil, one part by weight of lecithin, and 10 parts by weight of water were mixed at an ambient temperature, and then admixed with 100 parts by weight of powdery lipid-regulating agent prepared in Example A-5, and the mixture was powderized and shifted to make into powdery fat for regulating the amount of lipids. Since the product comprises CTS, lipids in the living body is regulated when one intakes foods and beverage, feed, pet food, etc., prepared with the product. Therefore, the product can be preferably used for the purpose of diet, preventing lifestyle-related disease, or as materials for foods of patients of lifestyle-related disease such as adiposis and hyperlipemia, requiring the restriction of intake of sugars and lipids, and for feeds or pet foods of animals which are required to regulate lipids in the body.

Example B-4

Vegetable Juice for Regulating the Amount of Lipids

To 97.5 parts by weight of commercial vegetable juice, one part by weight of partial xyloglucan hydrolyzate, one part by weight of lipid-regulating agent in a syrupy form, prepared in Example A-2, and 0.5 part by weight of glucosyl-naringin were added and dissolved to make into vegetable juice for regulating the amount of lipids. Since the product comprises CTS, its saccharide-derivative, partial xyloglucan hydrolyzate, glucosyl-naringin, and dietary fiber from vegetable, lipids in the living body are regulated when one intakes foods and beverage, feed, pet food, etc., prepared with the product. Therefore, the product can be preferably used for the purpose of diet, preventing lifestyle-related disease, or as a healthy supplement for patients of lifestyle-related disease such as adiposis and hyperlipemia, requiring the restriction of lipids intake. Further, since CTS and its saccharide-derivative decreases bad taste and smell of vegetable, the product is a vegetable juice easy to drink.

Example B-5

Beer for Regulating the Amount of Lipids

"NB BEER BASE SET", a commercial kit for preparing beer commercialized by Mail-Order Club of Tokyu Hands Inc., Tokyo, Japan, was purchased. Two parts by weight of lipid-regulating agent in a syrupy form, prepared by the method of Example A-1 was admixed with 100 parts by weight of the solution for fermentation in the kit and prepared beer according to the manual attached with the kit. Since the lipids in the living body are regulated by drinking the product, the product can be preferably used as a beer for the purpose of diet and preventing lifestyle-related disease. Further, since the product showed decreased bad taste and/or bad smell which is characteristic of beer, the product is a delicious beer with good aftertaste.

Example B-6

Shochu-Based Beverage for Regulating the Amount of Lipids

Four parts by weight of a lipid-regulating agent in a syrupy form, prepared by the method of Example A-1, and ume (Japanese apricot) flavor were admixed with a diluted shochu prepared by diluting commercial shochu with soda water and stirred to make into a shochu-based beverage with alcohol content of 6%. Since the lipids in the living body are regulated by drinking the product, the product can be preferably used as an alcohol beverage for the purpose of diet and preventing lifestyle-related disease. Further, since the product showed decreased bad taste and/or bad smell which is characteristic of shochu, the product is a delicious shochu-based beverage with good aftertaste.

Example B-7

Powdery Carrot Extract for Regulating the Amount of Lipids

Two parts by weight of hydrous crystalline trehalose and four parts by weight of a lipid-regulating agent in a syrupy form, prepared in Example A-1, were admixed with one part by weight of 5-folds concentrated carrot extract and dissolved by stirring. The resulting mixture was spray-dried by the conventional method to make into a powdery carrot extract for regulating the amount of lipids. Since the product comprises CTS and its saccharide-derivative, lipids in the living body are regulated when one intakes foods and beverage, feed, pet food, etc., prepared with the product. Therefore, the product can be preferably used for the purpose of diet, preventing lifestyle-related disease, or as a healthy supplement for patients of lifestyle-related disease such as adiposis and hyperlipemia, requiring the restriction of lipids intake.

Example B-8

Powdery Royal Jelly for Regulating the Amount of Lipids

Nine parts by weight of a lipid-regulating agent, prepared by mixing equal amount of crystalline CTS monohydrate and anhydrous crystalline CTS, both prepared in Example A-3, was admixed with one part by weight of frozen raw royal jelly and the mixture was pulverized by the conventional method to make into powdery raw royal jelly for regulating the amount of lipids. Since the product comprises CTS and royal jelly, lipids in the living body are regulated when one intakes foods and beverage, feed, pet food, etc., prepared with the product. Therefore, the product can be preferably used for the purpose of diet, preventing lifestyle-related disease, or as a healthy supplement for patients of lifestyle-related disease such as adiposis and hyperlipemia, requiring the restriction of lipids intake.

Example B-9

Chocolate Cookie for Regulating the Amount of Lipids

Chocolate cookie for regulating the amount of lipids was prepared by conventional method using 140 parts by weight of wheat flour (soft flour), 90 parts by weight of butter, 115 parts by weight of chocolate, 360 parts by weight of sucrose, 200 parts by weight of whole egg, 200 parts by weight of almond, and 50 parts by weight of a powdery lipid-regulating agent, crystalline CTS monohydrate prepared by the method of Example A-3. Since the lipids in the living body are regulated by CTS, the product can be preferably used for the purpose of diet and preventing lifestyle-related disease or as a confectionary for patients of lifestyle-related disease such as adiposis and hyperlipemia, requiring the restriction of lipids intake.

Example B-10

Jelly for Regulating the Amount of Lipids

Two hundred parts by weight of pureed raspberry, 46 parts by weight of sucrose, 12 parts by weight of a lipid-regulating agent in a syrupy form, prepared by the method of Example A-2, 50 parts by weight of starchy syrup, 122 parts by weight of "TREHA®", $\alpha,\alpha$-trehalose commercialized by Hayashibara Shoji Inc., Okayama, Japan, five parts by weight of pectin, three parts by weight of 50% citric acid aqueous solution, and 27 parts by weight of isomerized sugar were admixed with suitable amount of water and dissolved. The resulting solution was gradually boiled down to give a Brix value of about 78, put into a suitable mold, and cooled to an ambient temperature to make into a hard jelly for regulating the amount of lipids. Since CTS, its saccharide-derivative, and a dietary fiber, pectin regulate the lipids in the living body, the product can be preferably used for the purpose of diet and preventing lifestyle-related disease or as a confectionary for patients of lifestyle-related disease such as adiposis and hyperlipemia, requiring the restriction of lipids intake. Further, the product is a hard jelly having a good flavor with no syneresis.

Example B-11

Hard Candy for Regulating the Amount of Lipids

Sixty parts by weight of sucrose, 20 parts by weight of "TREHA®", $\alpha,\alpha$-trehalose commercialized by Hayashibara Shoji Inc., Okayama, Japan, and 1.5 parts by weight of a mixture of amino acids were admixed with 85 parts by weight of water, and then the resulting mixture was made into hard candy for regulating the amount of lipids by the conventional method. Since CTS and its saccharide-derivative regulate the lipids in the living body, the product can be preferably used for the purpose of diet and preventing lifestyle-related disease or as a confectionary for patients of lifestyle-related disease such as adiposis and hyperlipemia, requiring the restriction of lipids intake. Further, since bitter taste of amino acids is reduced by $\alpha,\alpha$-trehalose, CTS, and its saccharide-derivative, the product is a tasty candy comprising amino acids.

Example B-12

Rice Flour Bread for Regulating the Amount of Lipids

Four hundred parts by weight of "KOME-NO-KO (for bread)", rice flour premixed with gluten, commercialized by Saito Seifun Co., Ltd., Niigata, Japan, eight parts by weight of sodium chloride, 40 parts by weight of a powdery lipid-regulating agent comprising crystalline CTS pentahydrate as an effective ingredient, prepared in Example A-3, 12 parts by weight of sucrose, 12 parts by weight of skim milk, one part by weight of raw yeast, eight parts by weight of pullulan, and 320 parts by weight of water were mixed with stirring using a vertical mixer, and then 20 parts by weight of butter was further added to the mixture and kneaded to make into dough for bread. After fermenting the dough at 25° C. for 50 minutes, the dough was divided into suitable pieces and resulting doughs were kept at 35° C. for 50 minutes under the humidity conditions of 75%. Then, the fermented doughs were placed into a oven and baked for 40 minutes in the oven in which the upper- and lower temperature were controlled to 180° C. to make into rice bread for regulating the amount of lipids. Since the bread comprises CTS, lipids in the living body can be regulated by taking the product. Therefore, the product can be preferably used for the purpose of diet, preventing lifestyle-related disease, or as a meal for patients of lifestyle-related disease such as adiposis and hyperlipemia, requiring the restriction of lipids intake. Further, the product is delicious rice bread having a satisfactory flavor and mouthfeel.

Example B-13

Cooked Rice for Regulating the Amount of Lipids

Three hundred parts by weight of pre-washed and drained rice was soaked into a solution, prepared by dissolving 13.5 parts by weight of a powdery lipid-regulating agent which is prepared in Example A-4 into 375 parts by weight of water, for one hour. Then, the rice was cooked using a rice cooker to make into cooked rice for regulating the amount of lipids. Since the cooked rice comprises CTS, lipids in the living body can be regulated by taking the product. Therefore, the product can be preferably used for the purpose of diet, preventing lifestyle-related disease, or as a meal for patients of lifestyle-related disease such as adiposis and hyperlipemia, requiring the restriction of lipids intake.

Example B-14

Fish Paste for Regulating the Amount of Lipids

Two thousand parts by weight of fish meat of Alaska Pollock which is presoaked in water, 105 parts by weight of a powdery lipid-regulating agent, prepared by the method of Example A-5, three parts by weight of sodium lactate, and 0.2 part by weight of proanthocyanidin were mixed and the resulting mixture was minced and frozen at −20° C. to make into a frozen mince. After preserving at −20° C. for 90 days, the frozen mince was thawed. To the thawed mince, 100 parts by weight of an aqueous solution, prepared by dissolving 40 parts by weight of sodium glutamate, 100 parts by weight of potato starch, three parts by weight of sodium polyphosphate, 50 parts by weight of sodium chloride, and five parts by weight of sorbitol into 150 parts by weight of ice water, was added and the resulting mixture was mashed to make into paste. The resulting paste was divided to about 120 grams each, and shaped on the board. The shaped fish paste was steamed with taking 30 minutes to give an internal temperature of about 80° C. The steamed fish paste was cooled under the ambient temperature and preserved at 4° C. for 24 hours to produce a fish paste for regulating the amount of lipids. Since CTS and proanthocyanidin regulates the lipids in the living body, the product can be preferably used for the purpose of diet and preventing lifestyle-related disease, or as a food or its material for patients of lifestyle-related disease such as adiposis and hyperlipemia, requiring the restriction of lipids intake.

Example B-15

Bacon for Regulating the Amount of Lipids

Twenty two parts by weight of sodium chloride, four parts by weight of a lipid-regulating agent comprising crystalline CTS pentahydrate, prepared by the method of Example A-3, one part by weight of sucrose, two parts by weight of sodium lactate, two parts by weight of sodium polyphosphate, 0.5 part by weight of ascorbic acid, and 0.2 part by weight of sodium nitrite were admixed with 68.8 parts by weight of water and dissolved to make into a pickle solution. Nine parts by weight of rib of hog was soaked with one part by weight of the pickle solution uniformly with taking an enough time. The resulting rib of hog was smoked by the conventional method to make into bacon for regulating the amount of lipids. After smoking, the bacon was preserved at an ambient temperature for overnight and sliced. The resulting sliced bacon was packed under vacuum and preserved at 10° C. Since CTS regulates the lipids in the living body, the product can be preferably used for the purpose of diet and preventing lifestyle-related disease, or as a food material for patients of lifestyle-related disease such as adiposis and hyperlipemia, requiring the restriction of lipids intake.

Example B-16

Ice Cream for Regulating the Amount of Lipids

An ice cream was prepared by conventional method using 60 parts by weight of water, 12 parts by weight of non-fat milk, 12 parts by weight of sucrose, 5.5 parts by weight of "HALLODEX™", a saccharide composition comprising saccharide-derivatives of $\alpha,\alpha$-trehalose commercialized by Hyayashibara Shoji Inc., Okayama, Japan, 0.3 part by weight of gum, 0.5 part by weight of vanilla extract, and 11 parts by weight of a powdery anhydrous crystalline CTS prepared by the method of Example A-3. Since CTS regulates the lipids in the living body, the product can be preferably used for the purpose of diet and preventing lifestyle-related disease or as an ice cream for patients of lifestyle-related disease such as adiposis, hyperlipemia and diabetes, requiring the restriction of lipids intake. Although the product is produced without using fat (cream) which is usually used for preparing ice cream, the product has a creamy mouthfeel and taste similar with the case of a usual ice cream. Further, since the ice cream does not contain fat, it is a low calorie ice cream for regulating the amount of lipids.

Example B-17

Salad Dressing for Regulating the Amount of Lipids

A salad dressing was prepared by conventional method using 40 parts by weight of water, 20 parts by weight of white vinegar, 15 parts by weight of vegetable oil, five parts by weight of sucrose, two parts by weight of sodium chloride, one part by weight of garlic powder, 0.5 part by weight of onion powder, 0.1 part by weight of white pepper, 0.3 part by weight of gum and 15 parts by weight of a lipid-regulating agent, a powdery crystalline CTS pentahydrate prepared by the method of Example A-3. Since CTS regulates the lipids in the living body, the product can be preferably used for the purpose of diet and preventing lifestyle-related disease or as a salad dressing for patients of lifestyle-related disease such as adiposis, hyperlipemia and diabetes, requiring the restriction of lipids intake. Although the product is produced using about a half amount of vegetable oil which is used in a usual salad dressing, the product has a satisfactory mouthfeel and taste similar with the case of a usual salad dressing. Further, since the product comprises CTS, it has a characteristic of separating oil- and water-phases easily.

Example B-18

Tablet for Regulating the Amount of Lipids

Two hundred parts by weight of γ-oryzanol, 650 parts by weight of a lipid-regulating agent comprising crystalline CTS pentahydrate, prepared by the method of Example A-3, 50 parts by weight of glucosyl-hesperidin, and two parts by weight of magnesium stearate were mixed to homogeneity and the mixture was made into a 250 mg-tablet by the conventional method. Since γ-oryzanol, CTS, and glucosyl-hesperidin regulates the lipids in the living body, the product can be preferably used as a lipid-regulating agent for patients of adiposis, fatty liver and hyperlipemia.

Example B-19

Mixed Feed for Regulating the Amount of Lipids

Thirty parts by weight of wheat bran, 35 parts by weight of skim milk, 10 parts by weight of rice bran, 10 parts by weight of lactosucrose high content powder, 10 parts by weight of a multi-vitamin agent, five parts by weight of fish powder, five parts by weight of calcium monohydrogen-phosphate, three parts by weight of a liquid fat, three parts by weight of calcium carbonate, one part by weight of glucosyl-rutin, two parts by weight of sodium chloride, five parts by weight of a lipid-regulating agent in a syrupy form, prepared by the method of Example A-2, and two parts by weight of a mineral agent were mixed to make into a mixed feed for regulating the amount of lipids. Since CTS, its saccharide-derivative, and glucosyl-rutin regulates the lipids in the living body, the product can be preferably used as a feed to regulate lipids in the living body. The product is a feed or pet food for domestic animals, poultry, and pets, and is particularly preferable as a feed for pigs.

INDUSTRIAL APPLICABILITY

As described above, the present invention relates to a lipid-regulating agent comprising CTS, a non-reducing saccharide constructed by glucose, and/or its saccharide-derivative(s) as an effective ingredient(s) and a composition for regulating the amount of lipids comprising the lipid-regulating agent, where they can be used for regulating the amount of lipids of animals including human. Further, Since CTS and/or its saccharide-derivative (s) are safe even when one intakes orally and have satisfactory stability, the lipid-regulating agent comprising CTS and/or its saccharide-derivative(s) as an effective ingredient(s) of the present invention can be used in various fields such as foods and beverages, cosmetics, medicated cosmetics, pharmaceuticals, etc. The present invention, having these outstanding functions and effects, is a significantly important invention that greatly contributes to this art.

The invention claimed is:

1. A method for treating adiposis, which comprises administering a cyclic tetrasaccharide, represented by the formula of
cyclo{→6)-α-D-glucopyranosyl-(1→3)-α-D-glucopyranosyl-(1→6)-α-D-glucopyranosyl-(1→3)-α-D-glucopyranosyl-(1→},
to a patient in need thereof in an amount of 0.63 to 3.1 g/kg body weight a day, before or after taking meal.

2. The method of claim 1, wherein γ-oryzanol is administered together with said cyclic tetrasaccharide.

* * * * *